(12) United States Patent
Yasunaga

(10) Patent No.: US 10,416,127 B2
(45) Date of Patent: Sep. 17, 2019

(54) AUTOSAMPLER

(71) Applicant: Shimadzu Corporation, Kyoto (JP)

(72) Inventor: Kenichi Yasunaga, Kyoto (JP)

(73) Assignee: Shimadzu Corporation,
Nishinokyo-Kuwabaracho, Nakagyo-ku,
Kyoto-shi, Kyoto (JP)

( * ) Notice: Subject to any disclaimer, the term of this patent is extended or adjusted under 35 U.S.C. 154(b) by 186 days.

(21) Appl. No.: 15/563,425

(22) PCT Filed: May 28, 2015

(86) PCT No.: PCT/JP2015/065342
§ 371 (c)(1),
(2) Date: Sep. 29, 2017

(87) PCT Pub. No.: WO2016/189720
PCT Pub. Date: Dec. 1, 2016

(65) Prior Publication Data
US 2018/0088090 A1   Mar. 29, 2018

(51) Int. Cl.
| G01N 30/24 | (2006.01) |
| G01N 30/34 | (2006.01) |
| G01N 30/02 | (2006.01) |
| G01N 35/10 | (2006.01) |
| G01N 30/20 | (2006.01) |

(Continued)

(52) U.S. Cl.
CPC ............... *G01N 30/24* (2013.01); *G01N 1/00* (2013.01); *G01N 1/14* (2013.01); *G01N 30/02* (2013.01); *G01N 30/04* (2013.01); *G01N 30/20* (2013.01); *G01N 30/34* (2013.01); *G01N 35/1097* (2013.01); *G01N 2001/247* (2013.01); *G01N 2030/8804* (2013.01)

(58) Field of Classification Search
CPC ........ G01N 30/24; G01N 30/34; G01N 30/02; G01N 30/20; G01N 35/1097
USPC ........................................................... 73/61.55
See application file for complete search history.

(56) References Cited

U.S. PATENT DOCUMENTS

| 5,756,905 A * | 5/1998 | Ueda ...................... G01N 30/18 73/864.24 |
| 2012/0111127 A1 * | 5/2012 | Maeda ................... G01N 30/20 73/863.01 |

(Continued)

FOREIGN PATENT DOCUMENTS

| JP | 1983-050464 A | 3/1983 |
| JP | 1991-113361 A | 5/1991 |
| JP | 1998-170488 A | 6/1998 |

*Primary Examiner* — Clayton E. LaBalle
*Assistant Examiner* — Kevin C Butler
(74) *Attorney, Agent, or Firm* — Muir Patent Law, PLLC

(57) ABSTRACT

An autosampler is provided with a needle that has a capacity to retain a sample therein and has both ends each formed in a pointed shape, a first adapter that has an opening and causes the needle and a syringe pump to be in communication with each other through the insertion of the upper end part of the needle into the opening, and a second adapter that connects the needle and a mobile-phase liquid-delivery flow path using a structure similar to that of the first adapter. The autosampler is configured such that the first adapter and the second adapter are attached to and removed from the upper end part of the needle so as to create flow paths including the needle as necessary and carry out a sampling operation and injecting operation.

5 Claims, 12 Drawing Sheets

(51) Int. Cl.
*G01N 1/00* (2006.01)
*G01N 1/14* (2006.01)
*G01N 30/04* (2006.01)
*G01N 1/24* (2006.01)
*G01N 30/88* (2006.01)

(56) References Cited

U.S. PATENT DOCUMENTS

| | | | |
|---|---|---|---|
| 2014/0318274 A1* | 10/2014 | Zimmerman | B01D 15/14 |
| | | | 73/863 |
| 2016/0054274 A1* | 2/2016 | Cormier | G01N 30/20 |
| | | | 73/61.55 |
| 2016/0069844 A1* | 3/2016 | Jackson | G01N 30/06 |
| | | | 73/61.55 |
| 2016/0153942 A1* | 6/2016 | Yotani | G01N 30/16 |
| | | | 73/61.55 |
| 2016/0274069 A1* | 9/2016 | Fujita | G01N 30/20 |
| 2018/0088090 A1* | 3/2018 | Yasunaga | G01N 1/14 |

* cited by examiner

AUTOSAMPLER

TECHNICAL FIELD

The present invention relates to an autosampler configured to collect a sample to be analyzed with a liquid chromatograph from a sample container and inject it into an analysis flow path communicated with an analytical column.

BACKGROUND TECHNIQUE

In an analysis using a liquid chromatograph, an autosampler is used to automatically introduce a plurality of samples into analytical columns in a predetermined order. As an autosampler, an autosampler adopting a so-called total-volume injection method is widely used in which a predetermined amount of sample is collected from a sample container and the total volume thereof is injected into an analysis flow path through which a mobile phase flows.

In injecting a sample by a total-volume injection method, initially, a predetermined amount of sample is sucked from a sample container with a needle and is retained in a sample loop connected to a base end portion of the needle. Thereafter, the needle is inserted into a sample injection port and a flow path switching operation by a flow path switching valve is performed to thereby interpose the sample loop between a liquid feeding device that feeds a mobile phase and an analytical column. With this, the entire sample retained in the sample loop is transferred to and introduced into the analytical column by the mobile phase from the sample container (see Patent Document 1).

As other injection methods, there are some injection methods adopting a fixed loop injection method. In the method, a predetermined amount of sample is sucked from a sample container through a needle and retained in a sample loop for sucking a sample connected to a base end portion of the needle. After that, the needle is inserted into a sample injection port to retain a necessary amount of sample in the sample loop for a sample injection connected via a flow path switching valve. Thereafter, by performing a switching flow path operation by the flow path switching valve, the sample loop for a sample injection is interposed between a liquid feeding device for feeding a mobile phase and an analytical column. As a result, the sample retained in the sample loop for a sample injection is transferred to and introduced into the analytical column by the mobile phase from the sample container.

The above-described two injection methods have the following advantages and disadvantages. In the total-volume injection method, since the entire amount of sample retained in the sample loop is injected into the analysis flow path, there is a merit that there is no sample loss. On the other hand, in the fixed loop injection method, since a part of the sample retained in the sample loop for a sample injection is discarded, it is particularly disadvantageous in the case of a valuable sample.

Further, in the total-volume injection method, the flow path connected to the base end portion of the needle is formed long to ensure the mobility of the needle, resulting in a large dead volume, which in turn causes disadvantages that a sample diffusion and a gradient delay are likely to occur. On the other hand, in the fixed loop injection method, the sample loop for a sample injection is formed independent of the needle. Therefore, there are merits that a dead volume is smaller than that in the total-volume injection method, the peak of the chromatogram becomes shaper than that of the total-volume injection method, and the analysis speed is high.

PRIOR ART

Patent Document

Patent Document 1: Japanese Unexamined Patent Application Publication No. H10-170488

SUMMARY OF THE INVENTION

Problems to be Solved by the Invention

In either of the above-described total-volume injection method and fixed loop injection method, the maximum amount of sample that can be analyzed by introducing into the analytical column is determined by the capacity of the sample loop. Therefore, depending on the injection volume of the sample, the sample loop for a sample injection needs to be replaced with a sample loop having an optimal capacity. However, when replacing the sample loop, it is required to remove the fitting used to connect the sample loop once and then replace it with another sample loop, and therefore the work is complicated.

Under the circumstances, an object of the present invention is to facilitate an exchange of a capacity for temporarily retaining a sample to be introduced into an analytical column and reduce a dead volume within an autosampler.

Means for Solving the Problems

One embodiment of an autosampler according to the present invention includes a needle, a needle driving mechanism, an injection port, a syringe pump, a first adapter, a mobile-phase liquid-delivery flow path, a first adapter driving mechanism, a second adapter, a second adapter driving mechanism, a switching mechanism, and a control unit.

The needle has a capacity to retain a sample therein, and both ends thereof are each formed in a pointed shape. The needle driving mechanism is configured to hold the needle in a vertical direction and moves it in the vertical direction and a horizontal plane direction. The injection port has an opening opened upward for allowing insertion of a lower end portion of the needle and is configured to connect the needle by being inserted by the lower end portion of the needle in the opening. The syringe pump is configured to perform suction and discharge of a liquid. The first adapter has an opening in communication with a suction/discharge opening of the syringe pump and opened downward for allowing insertion of an upper end portion of the needle. The first adapter is configured to connect the needle by being inserted by the upper end portion of the needle in the opening to connect the syringe pump and the needle. The mobile-phase liquid-delivery flow path is for delivering a mobile phase. The second adapter is connected to the mobile-phase liquid-delivery flow path and has an opening opened downward for allowing insertion of the upper end portion of the needle. The second adapter is configured to connect the needle with the upper end portion of the needle inserted into the opening to communicate the mobile-phase liquid-delivery flow path and the needle. The first adapter driving mechanism is configured to perform attachment/detachment of the first adapter with respect to the upper end portion of the needle by moving the first adapter in the vertical direction above the needle. The second adapter driving mechanism is configured to perform attachment/detachment of the second adapter with respect to the upper end portion of the needle by moving the second adapter in the vertical direction above the needle with the lower end inserted in the injection port.

The switching mechanism is configured to switch whether to connect a liquid feeding device for feeding the mobile phase to the mobile-phase liquid-delivery flow path and whether to connect between an analysis flow path in communication with an analytical column which separates the sample by a component and the injection port. The switching mechanism has an injecting mode in which the liquid feeding device is connected to the mobile-phase liquid-delivery flow path and at the same time the analysis flow path and the injection port are in communication with each other.

The control unit is configured to control the needle driving mechanism, the syringe pump, the first adapter driving mechanism, the second adapter driving mechanism, and the switching mechanism. The control unit includes a sampling operation unit configured to perform a sampling operation in which the upper end portion of the needle is connected to the first adapter, the lower end portion of the needle is inserted into a sample container containing the sample to be sucked, and the sample is sucked into the needle by the syringe pump, a needle movement operation unit configured to perform a needle movement operation in which after the sampling operation, the lower end portion of the needle is connected to the injection port in a state in which the upper end portion of the needle is connected to the first adapter, and an injecting operation unit configured to perform an injecting operation in which after the needle movement operation, the first adapter is detached from the upper end portion of the needle, the second adapter is connected to the upper end portion of the needle, and the switching mechanism is set to the injecting mode.

Effects of the Invention

In one embodiment of the autosampler according to the present invention, a needle having a capacity to retain a sample in an inner side thereof and having both ends each formed in a pointed shape is used, and when the injection port, the first adapter, and the second adapter are detachably attached to the end portion of the needle, a flow path including the needle is formed. Therefore, the sample loop for temporarily retaining a sample becomes unnecessary, and therefore a dead volume can be reduced. Further, a complicated work of exchanging the sample loop becomes unnecessary.

EMBODIMENTS FOR CARRYING OUT THE INVENTION

The needle driving mechanism is preferably equipped with a needle holding unit which detachably holds the needle. With this, it is possible to replace a needle with another needle different in capacity, which facilitates a change of a holding capacity of a sample.

It is preferable that the needle driving mechanism be further provided with a needle setting unit for setting a plurality of needles different in internal capacity and that the needle driving mechanism be configured to hold one needle among the needles set in the needle setting unit with a needle holding unit depending on a sample injection volume to be injected to an analysis flow path. In this case, a needle having an appropriate internal capacity is automatically used depending on a sample injection amount set by a user.

As an example of a configuration of holding the needle with the needle holding unit, the following configuration can be exemplified. That is, the needle has a protrusion formed on the outer peripheral surface of the needle so as to protrude in the peripheral direction, and the needle holding unit has a recess for holding the needle by fitting the protrusion on the upper surface from above and a cutout portion formed from a side surface to the center of the recess and having a width larger than the diameter of the needle and smaller than the inner diameter of the recess. With this configuration, the mounting of the needle on the needle holding unit can be completed by merely moving the needle holding unit and the needle relative to each other so that a portion of the needle lower than the protrusion passes the cutout portion and reaches the center of the recess and thereafter raising the needle holding unit relative to the needle so that the protrusion is fitted in the recess. Further, the removal of the needle from the needle holding unit can be completed by merely lowering the needle holding unit relative to the needle so that the protrusion is detached from the recess and thereafter moving the needle and the needle holding unit relatively in a horizontal direction so that the needle passes through the cutout portion. As described above, the needle attachment/detachment relative to the needle holding unit can be performed easily.

As a second adapter driving mechanism, a mechanism configured to move a second adapter in a vertical direction above an injection port can be exemplified. In this case, a first adapter driving mechanism includes a mechanism for moving a first adapter in the vertical direction above the needle and a mechanism for retracting the first adapter from above the needle when the lower end portion of the needle is connected to the injection port.

Figure 1:
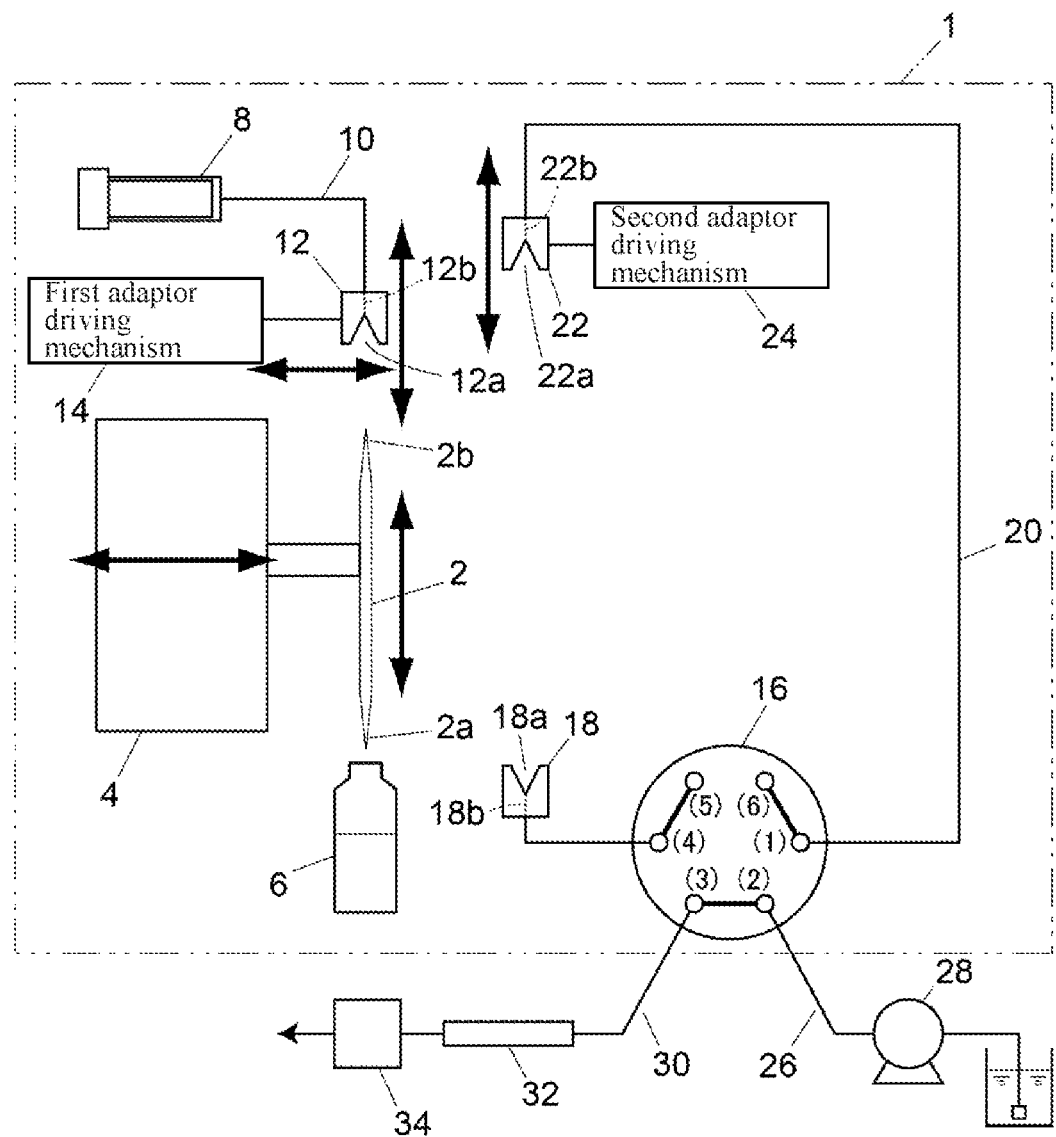
FIG. 1 is a schematic configuration diagram showing an example of an autosampler together with a liquid chromatograph.

A configuration of an embodiment of the autosampler will be described with reference to FIG. 1.

A needle 2 for sucking a sample from a sample container 6 is held in a vertically oriented state by a needle driving mechanism 4. In the autosampler 1 of this example, it is configured such that one end portion of a syringe flow path 10 or a mobile-phase liquid-delivery flow path 20 can be attached/detached to/from an upper end portion 2b of the needle 2. A first adapter 12 is provided at one end portion of the syringe flow path 10, and a second adapter 22 is provided at one end portion of the mobile-phase liquid-delivery flow path 20. By attaching/detaching the first adapter 12 or the second adapter 22 to/from the upper end portion 2b of the needle 2, the attachment/detachment of one end portion of the syringe flow path 10 or the mobile-phase liquid-delivery flow path 22 to/from the needle 2 is performed. The upper end portion 2b of the needle 2 is formed in a pointed shape in the same manner as in the lower end portion 2a so that the attachment/detachment of the first adapter 12 and the second adapter 22 can be performed. The structure of the first adapter 12 and that of the second adapter 22 will be described later.

The first adapter 12 is moved in the horizontal plane direction and the vertical direction by a first adapter driving mechanism 14. The second adapter 22 is provided above an injection port 18, which will be described later, and is moved in the vertical direction by a second adapter driving mechanism 24.

Figure 3:
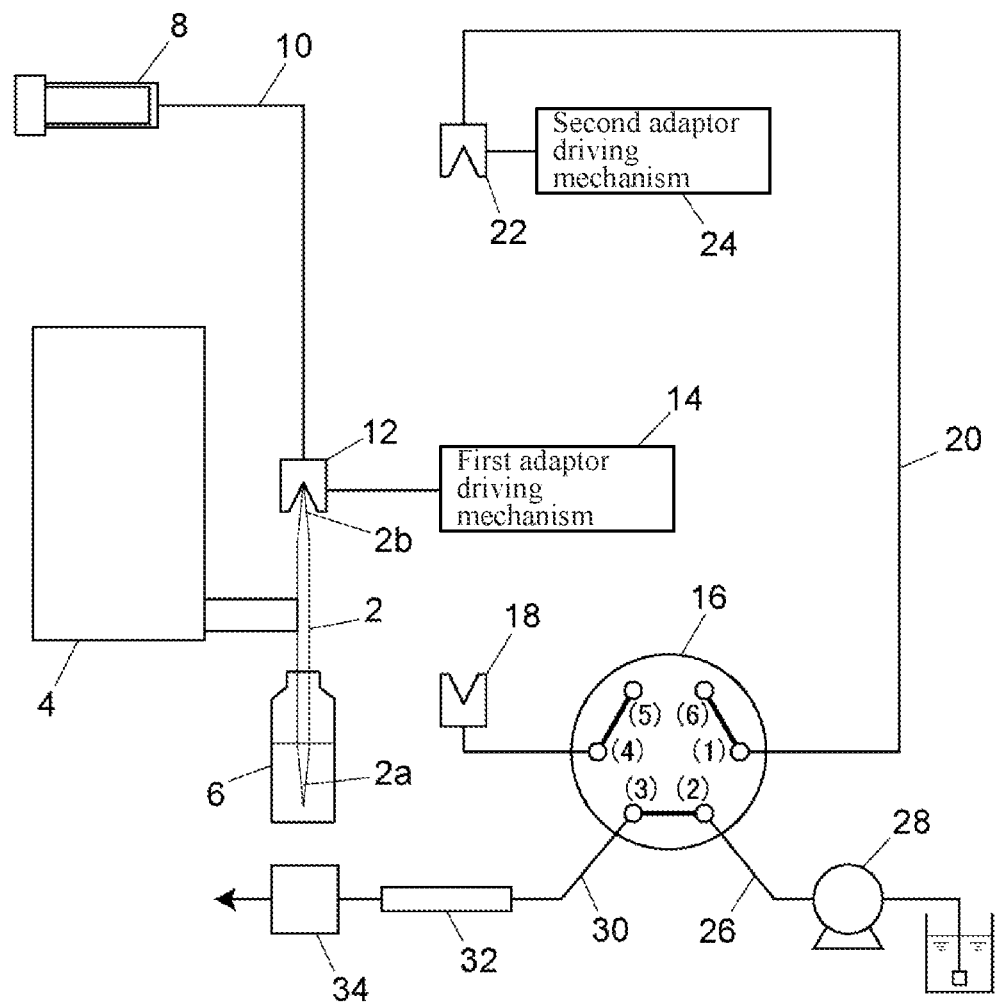
FIG. 3 is a schematic configuration diagram showing a state at the time of sample suction in the example.

The other end of the syringe flow path 10 is communicated with a suction/discharge port of a syringe pump 8 for sucking and ejecting a liquid or a gas. With this, by attaching the first adapter 12 to the upper end portion 2b of the needle 2, the needle 2 and the syringe pump 8 can be communicated with each other. When sucking a sample from the sample container 6, as shown in FIG. 3, the first adapter 12 is attached to the upper end portion 2b of the needle 2 so that the needle 2 and the syringe pump 8 are communicated with each other, and the lower end portion 2a of the needle 2 is inserted in the container 6. Then, the syringe pump 8 is driven to perform a suction operation to retain the sample sucked in the needle 2. In order to retain the sample sucked from the lower end portion 2a of the needle 2 in the needle 2, as the needle 2, a needle having an internal capacity equal to or greater than the suction amount of the sample at that time is used.

The other end of the mobile-phase liquid-delivery flow path 20 is connected to a port (1) of a switching valve 16. The flow path 20 is a mobile-phase liquid-delivery flow path for delivering a mobile phase supplied by a liquid feed pump 28 which will be described later. The switching valve 16 is a 6-way valve having six ports (1) to (6). To the port (2), a mobile phase supply flow path 26 is connected. To the port (3) adjacent to the port (2), an analysis flow path 30 communicated with an analytical column 32 and a detector 34 is connected. Furthermore, a port (4) adjacent to the port (3) is communicated with the injection port 18. The injection port 18 connects the port (4) of the switching valve 16 and the needle 2 by being inserted by the lower end portion 2a of the needle 2. The ports (5) and (6) of the switching valve 16 are closed ports. None of the ports is connected to any flow path, nor are they open to the atmosphere.

The switching valve 16 is a 2-position valve for switching the connection between adjacent ports, and serves as a switching mechanism for selectively connecting the mobile phase supply flow path 26 to either the mobile-phase liquid-delivery flow path 20 side or the analysis flow path 30 side. In FIG. 1, it shows a state in which the port (1) and the port (6) are connected, the port (2) and the port (3) are connected, and the port (4) and the port (5) are connected. Hereinafter, this state of the switching valve 16 will be referred to as a loading mode. On the other hand, the state of the switching valve 16 in which the port (1) and the port (2) are connected, the port (3) and the port (4) are connected, and the port (5) and port (6) are connected will be referred to as an injecting mode.

Figure 5:
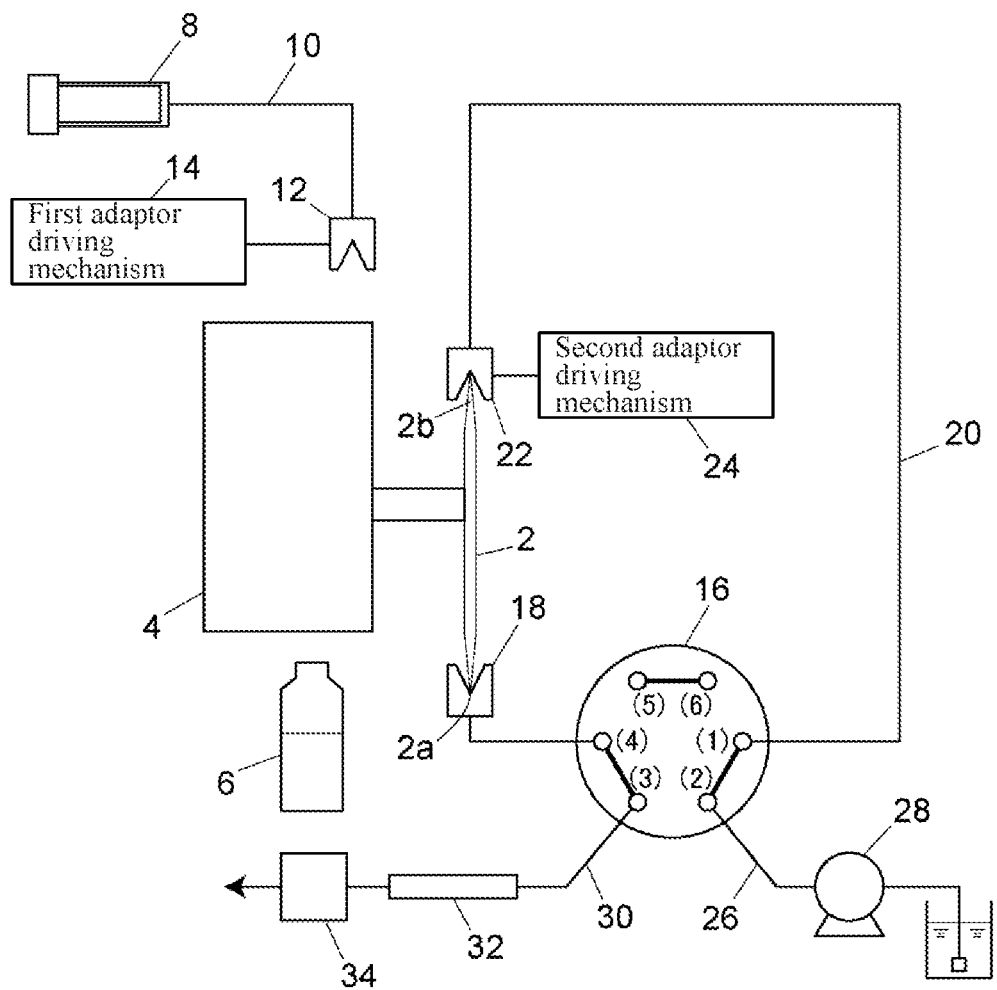
FIG. 5 is a schematic configuration diagram showing a state at the time of sample injection in this example.

In a state in which the first adapter 12 is attached to the upper end portion 2b of the needle 2 after sucking the sample in the needle 2 (see FIG. 3), the needle 2 retaining the sample can be pulled out of the sample container 6 and moved to the position of the injection port 18. In a state in which the lower end portion 2a of the needle 2 is inserted into the injection port 18 and the second adapter 22 is connected to the upper end portion 2b of the needle 2, when the switching valve 16 is switched from the loading mode to the injecting mode, as shown in FIG. 5, the mobile phase supplied by the liquid feed pump 28 flows through the needle 2 via the mobile-phase liquid-delivery flow path 20. As a result, the sample in the needle 2 is introduced to the analysis flow path 30 via the injection port 18.

Figure 7:
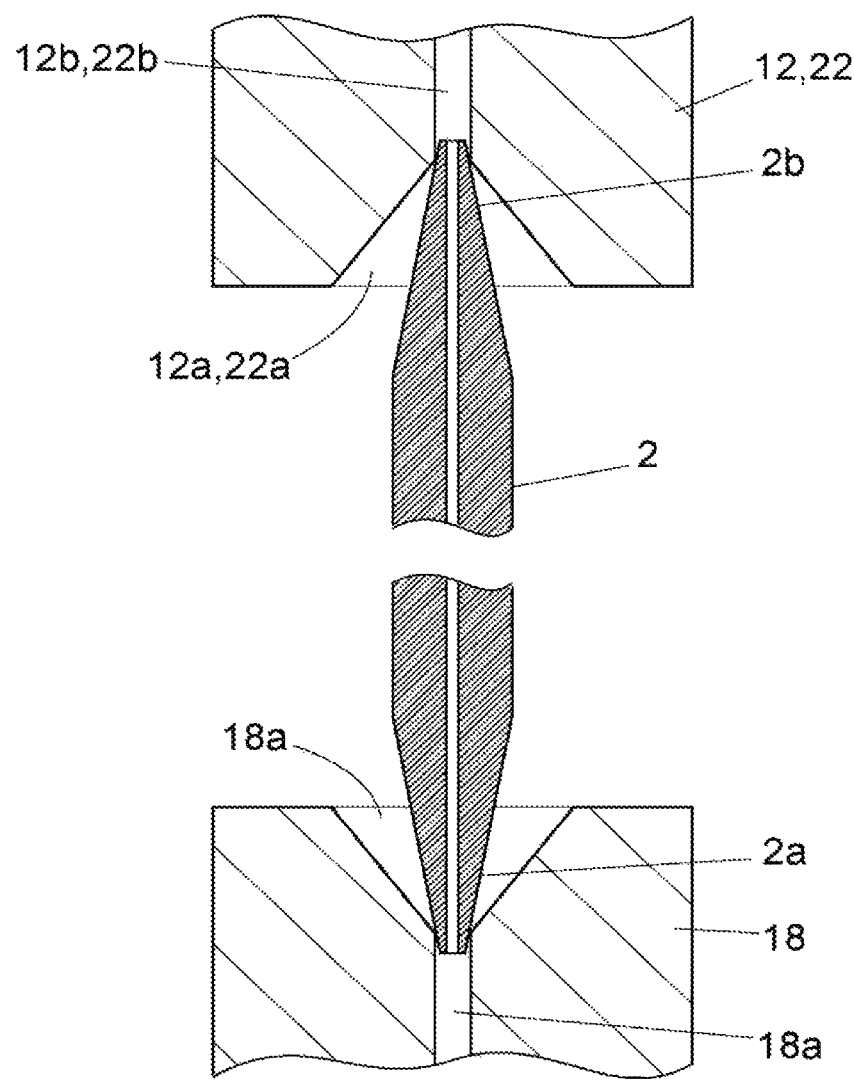
FIG. 7 is a cross-sectional view showing an example of a structure of an injection port and that of an adapter in the example.

Here, the first adapter 12, the second adapter 22, and the injection port 18 will be described with reference to FIG. 7.

The first adapter 12 and the second adapter 22 are each provided with an opening 12a and 22a opened downward. The inner peripheral surface of the opening 12a and 22a is inclined so that its inner diameter increases as it advances downward, and the inclination angle thereof is larger than the inclination angle of the outer peripheral surface of the upper end portion 2b of the needle 2. At the bottom portion of the opening 12a and 22a, an end portion of the flow path 12b and 22b communicated with the syringe flow path 10 and the mobile-phase liquid-delivery flow path 22 is provided. The inner diameter of the flow path 12b and 22b is larger than the outer diameter of the tip end of the upper end portion 2b of the needle 2. When a part of the tip end side of the upper end portion 2b of the needle 2 is inserted into the flow path 12b and 22b, the edge of the flow path 12b and 22b comes into line contact with the outer peripheral surface of the upper end portion 2b, so that the liquid tightness can be enhanced at the time of connecting the needle 2.

The injection port 18 is provided with an opening 18a opened upward, and an end portion of the flow path 18b communicated with the port (4) of the switching valve 16 is provided at the bottom portion of the opening 18a. In the same manner as in the first adapter 12 and the second adapter 22, the injection port 18 also has a structure for enhancing the liquid tightness at the time of connecting the needle 2 by a line contact between the outer peripheral surface of the lower end portion 2a of the needle 2 and the edge of the flow path 18b.

Figure 2:
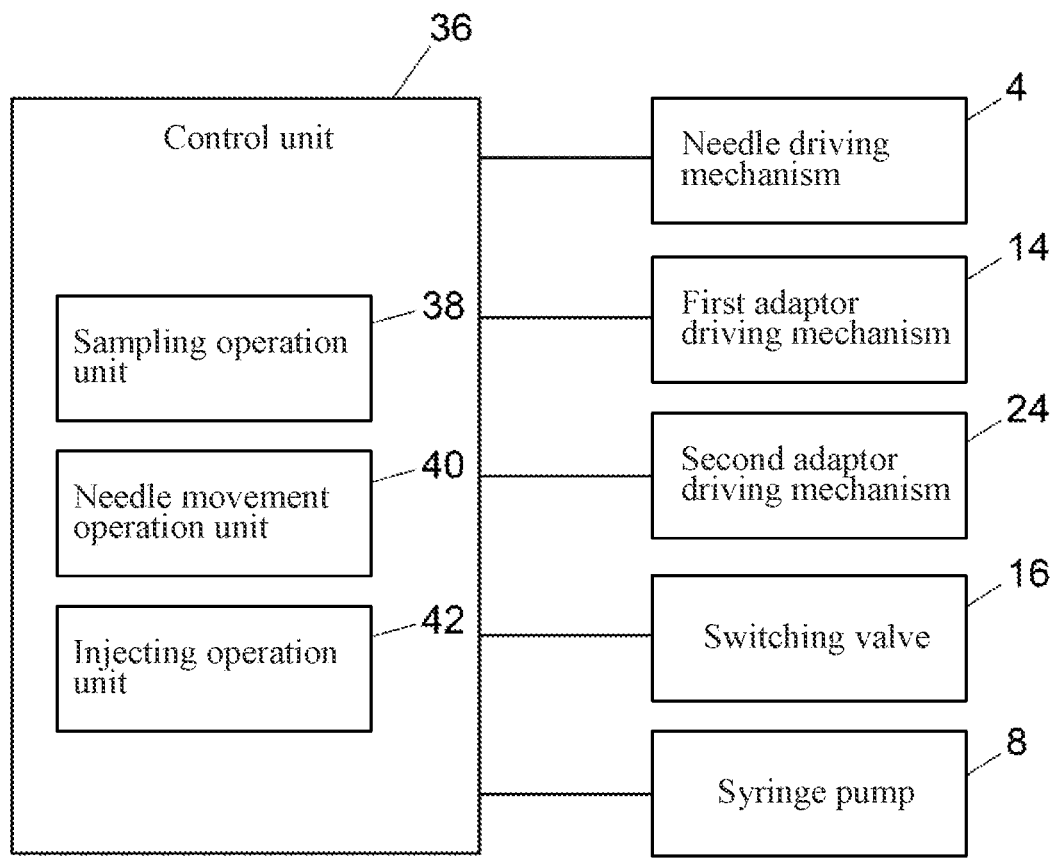
FIG. 2 is a block diagram showing a control system in the example.

As shown in FIG. 2, the autosampler 1 is provided with a control unit 36 for controlling operations of the needle driving mechanism 4, the first adapter driving mechanism 14, the second adapter driving mechanism 24, the switching valve 16, and the syringe pump 8. The control unit 36 is provided with a sampling operation unit 38, a needle movement operation unit 40, and an injecting operation unit 42. The sampling operation unit 38 is configured to perform a sampling operation to suck the sample into the needle 2. The needle movement operation unit 40 is configured to execute an operation of moving the needle 2 to the injection port 18 after completion of the sampling operation. The injecting operation unit 42 is configured to connect the second adapter 22 to the upper end portion of the needle 2 and switch the switching valve 16 to the injecting mode after completion of the needle moving operation. The control unit 36 is composed of, for example, a computer and a storage device for storing information provided inside the autosampler 1. The sampling operation unit 38, the needle movement operation unit 40, and the injecting operation unit 42 are functions obtained by executing a program stored in the storage device constituting the control unit 36 by a computer.

Figure 6:
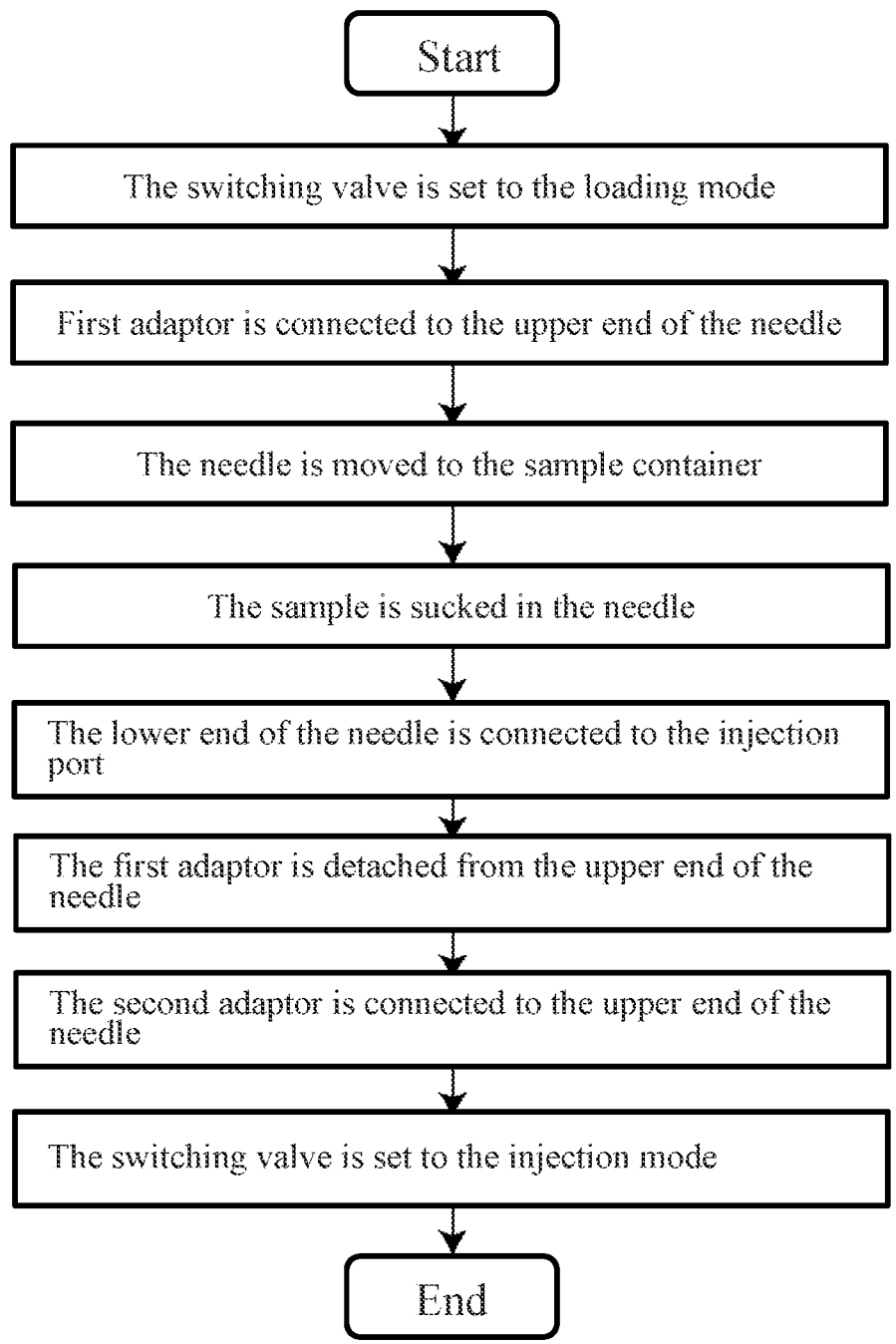
FIG. 6 is a flowchart showing a series of operations of sample injection in the example.

A series of sample injection operations in the autosampler 1 of this example will be described with reference to FIGS. 3 to 5 and the flowchart of FIG. 6.

In the autosampler 1, before sucking the sample from a desired sample container 6, as shown in FIG. 5, the second adapter 22 is connected to the upper end portion 2b of the needle 2, the lower end portion of the needle 2 is connected to the injection port 18, the switching valve 16 is in the injecting mode, and the mobile phase is flowing through the needle 2. At the timing of injecting a sample, as shown in FIG. 3, after switching the switching valve 16 to the loading mode, the second adapter 22 is detached from the upper end portion 2b of the needle 2, and the first adapter 12 is connected to the upper end portion 2b of the needle 2. In that state, the needle 2 is moved to the position of a desired sample container 6 and the lower end portion 2a of the needle 2 is inserted into the sample container 6. Then, the syringe pump 8 performs the suction operation, so that the prescribed amount of the sample is retained in the needle 2.

Figure 4:
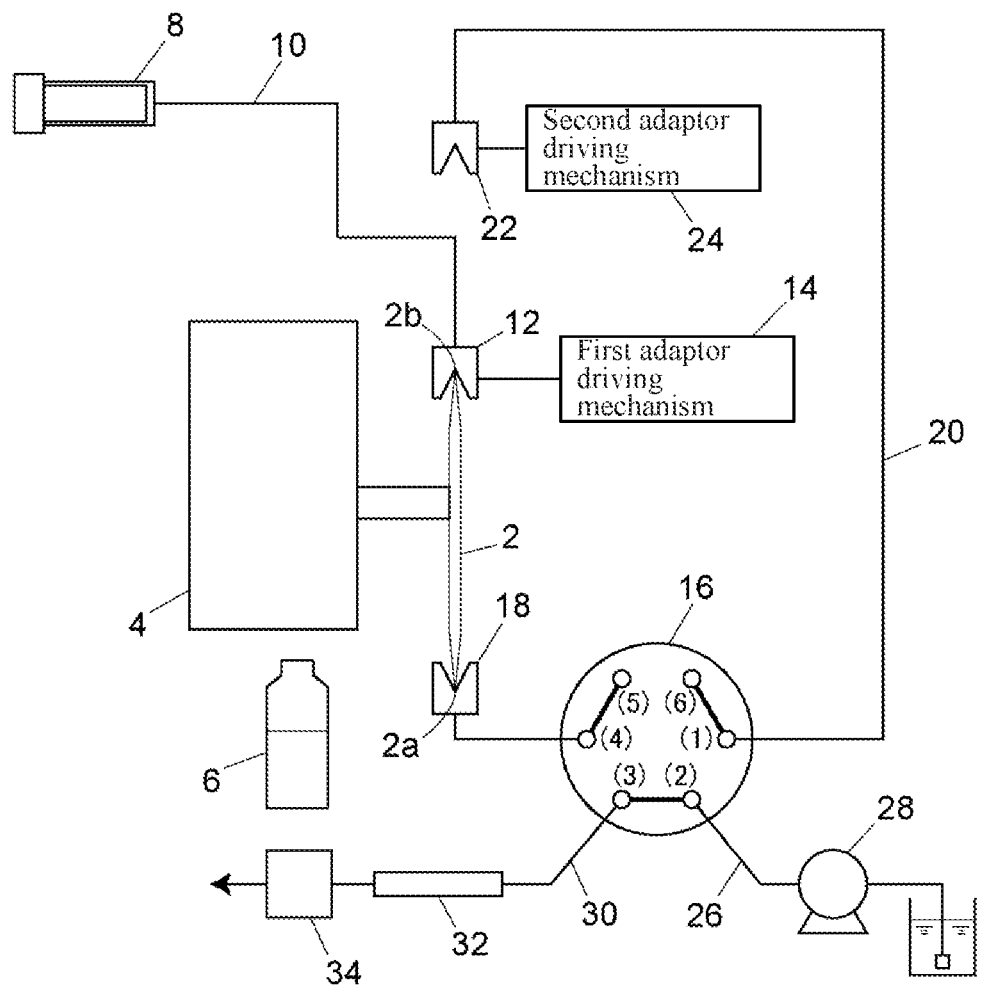
FIG. 4 is a schematic configuration diagram showing a state at the time of transition to sample injection after sample suction in the example.

Next, as shown in FIG. 4, in a state in which the first adapter 12 is connected to the upper end portion 2b of the needle 2, the needle 2 is pulled out of the sample container 6 and moved to the position of the injection port 18 to connect the lower end portion 2a of the needle 2 to the injection port 18. In this state, the first adapter 12 is detached from the upper end portion 2b of the needle 2 and retracted from the position above the needle 2. At this time, since the switching valve 16 is in the loading mode, the port (4) communicated with the injection port 18 is communicated with the closed port (5). Therefore, even if the first adapter 12 is detached from the upper end portion 2b of the needle 2, the sample is kept retained in the needle 2.

Thereafter, as shown in FIG. 5, the second adapter 22 is connected to the upper end portion 2b of the needle 2, and the switching valve 16 is switched to the injecting mode. The switching valve 16 is switched to the injecting mode so that the mobile-phase liquid-delivery flow path 20 and the needle 2 are interposed between the mobile phase supply flow path 26 and the analysis flow path 30. As a result, the mobile phase from the mobile phase supply flow path 26 is supplied to the needle 2 via the mobile-phase liquid-delivery flow path 20, and the sample in the needle 2 is introduced to the analysis flow path 30. The sample introduced into the analysis flow path 30 is separated for each component in the analytical column 32 and detected by the detector 34.

Figure 8:
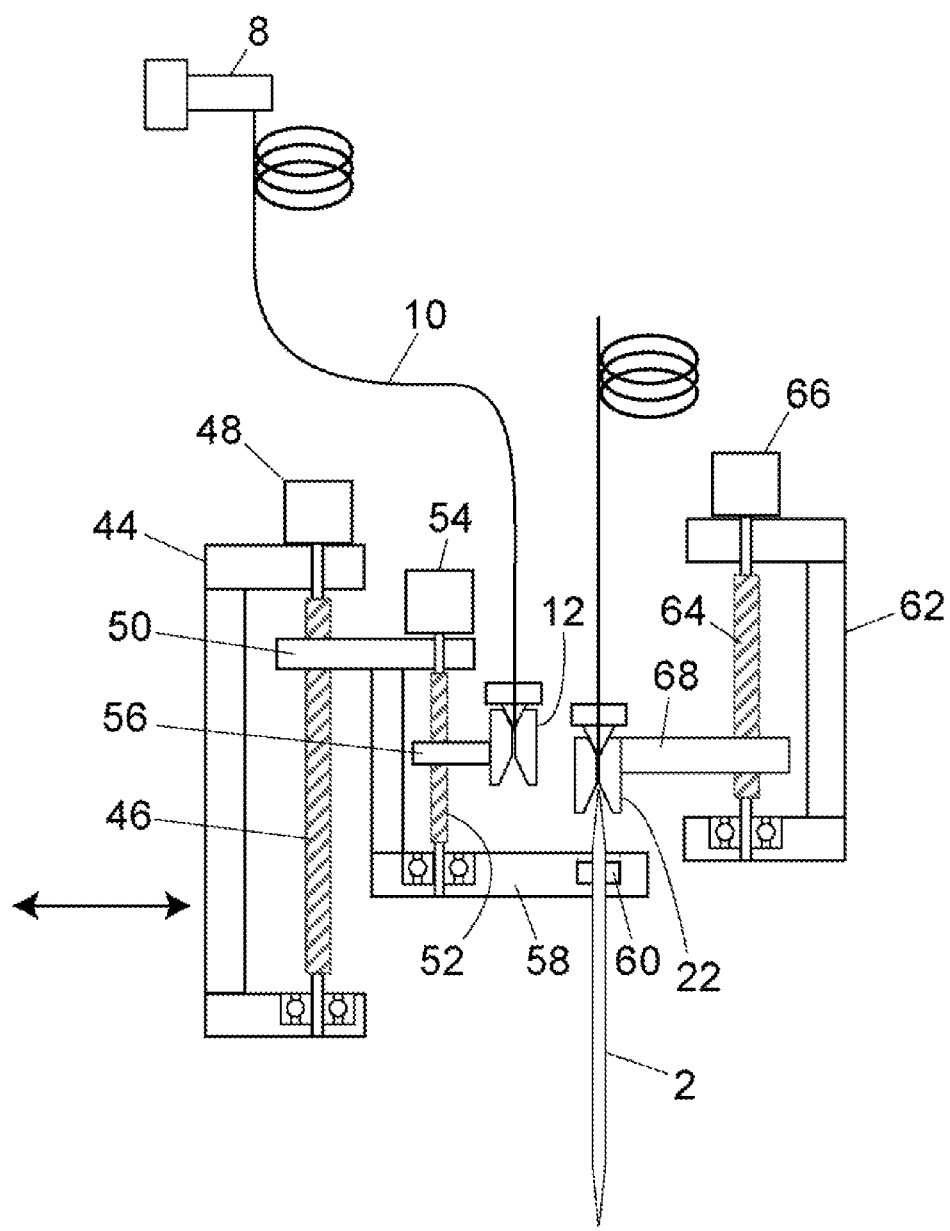
FIG. 8 is a diagram showing an example of a configuration realizing a needle driving mechanism, a first adapter driving mechanism, and a second adapter driving mechanism in the example.

Next, one example of the configuration realizing the needle driving mechanism 4, the first adapter driving mechanism 14, and the second adapter driving mechanism 24 will be described with reference to FIGS. 8 and 9.

A ball screw 46 arranged in the vertical direction is supported by a horizontal moving unit 44 which moves in a horizontal plane direction. The ball screw 46 is rotated by a motor 48. A first horizontal arm 50 extending in the horizontal direction is attached to the ball screw 46. The first horizontal arm 50 is configured to move in the vertical direction along the ball screw 46 without rotating as the ball screw 46 rotates.

Below the first horizontal arm 50, a needle holding arm 58 extending in the horizontal direction is provided at a distance from the first horizontal arm 50. The needle holding arm 58 is fixed to the first horizontal arm 50 and is configured to move in the vertical direction together with the first horizontal arm 50. The needle 2 is detachably held on the tip end side of the needle holding arm 58. The structure in which the needle holding arm 58 detachably holds the needle 2 will be described later.

The horizontal moving unit 44, the ball screw 46, the motor 48, the first horizontal arm 50, and the needle holding arm 58 configure the needle driving mechanism 4.

A ball screw 52 arranged in the vertical direction is supported between the first horizontal arm 50 and the needle holding arm 58. The ball screw 52 is rotated by a motor 54. A second horizontal arm 56 extending in the horizontal direction is attached to the ball screw 52. The second horizontal arm 56 is configured to move in the vertical direction along the ball screw 52 without rotating as the ball screw 52 rotates.

Figure 9:
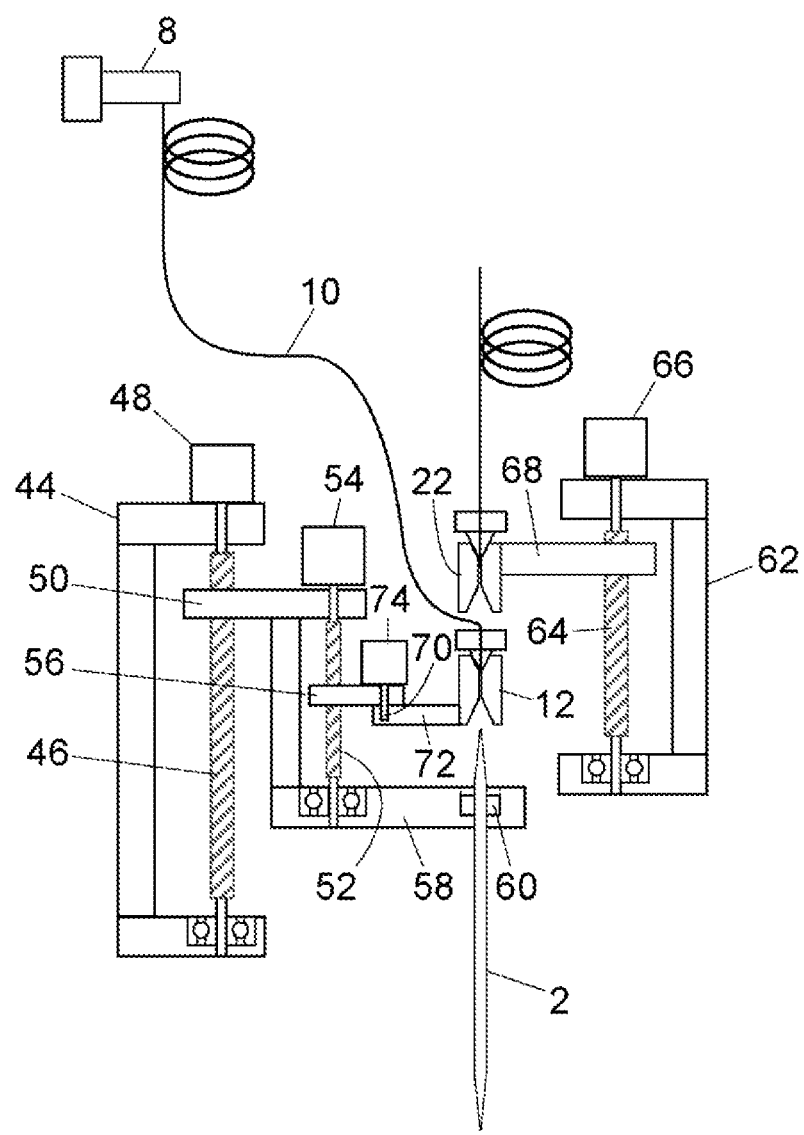
FIG. 9 is a diagram showing a state in which a first adapter is arranged above the needle in the above-described configuration.

As shown in FIG. 9, a first adapter holding arm 72 extending in the horizontal direction is attached to the tip end portion of the second horizontal arm 56 so as to be rotatable in the horizontal plane centering a rotation shaft 70. The rotation shaft 70 is rotated by the motor 74. The first adapter holding arm 72 is attached to the tip end portion of the first adapter holding arm 72, so that the rotation of the first adapter holding arm 72 causes either the state in which the first adapter 12 is deviated from the position directly above the needle 2 (the state shown in FIG. 8) or the state in which the first adapter 12 is located directly above the needle 2 (the state shown in FIG. 9).

The horizontal moving unit 44, the ball screw 46, the motor 48, the first horizontal arm 50, the ball screw 52, the motor 54, the second horizontal arm 56, and the first adapter holding arm 72 realize the first adapter driving mechanism 14. With this configuration, in a state in which the first adapter 12 is connected to the upper end portion of the needle 2, the needle 2 can be moved to the position of the injection port 18 or the desired position of the sample container 6, and if necessary, the first adapter 12 can be retracted from the position directly above the needle 2.

The second adapter driving mechanism 24 for moving the second adapter 22 in the vertical direction at a position directly above the injection port 18 is realized by the ball screw support portion 62, the ball screw 64, the motor 66, and the second adapter holding arm. The ball screw support portion 62 supports the ball screw 64 in the vertical direction in a rotatable manner. The ball screw 64 is rotated by the motor 66. The second adapter holding arm 68 moves in the vertical direction along the ball screw 64 as the ball screw 64 rotates.

Next, a structure in which the needle holding arm 58 detachably holds the needle 2 will be described with reference to FIGS. 10 to 12.

Figure 10:
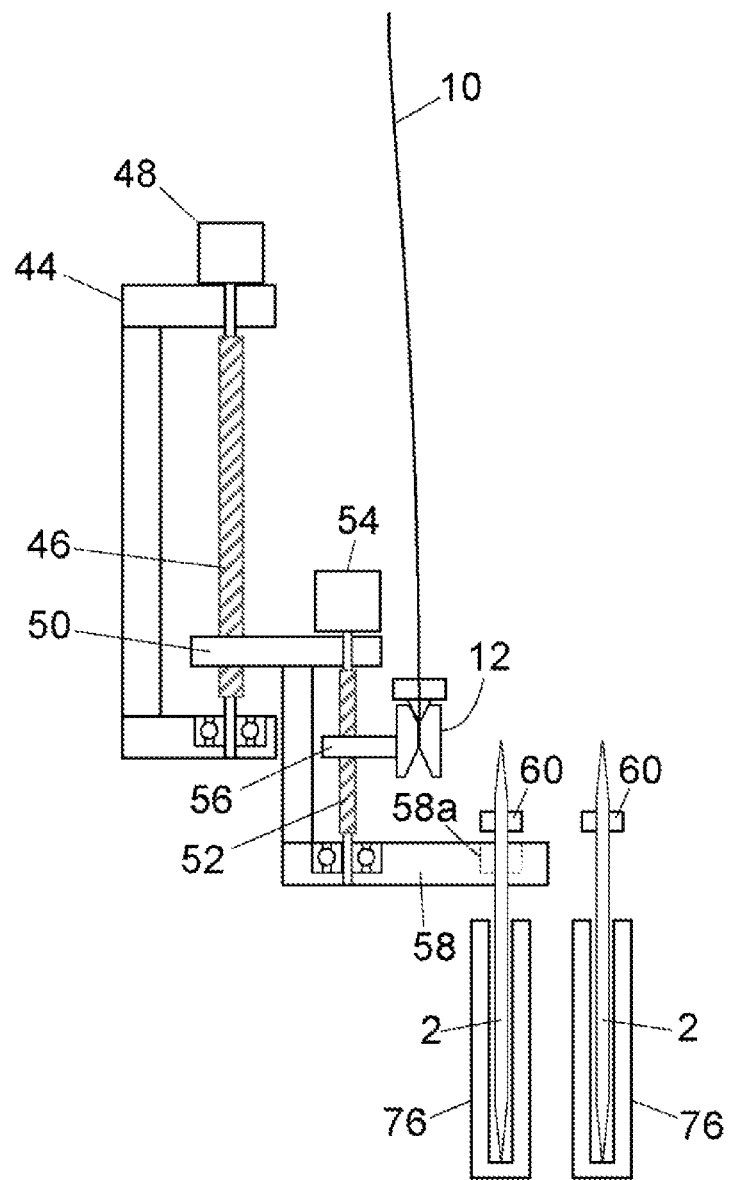
FIG. 10 is a diagram schematically showing a configuration for automatically attaching/detaching the needle.

As shown in FIG. 10, the autosampler of this example is provided with needle setting units 76 in which a plurality of needles 2 different in internal capacity is installed within the movement range of the needle holding arm 58 in the apparatus. The needle setting unit 76 has a vertical hole that accommodates the lower part of the needle 2. The upper part of the needle 2 protrudes upward from the hole of the needle setting unit 76. An annular ring 60 protruding in the outer peripheral direction is provided as a protrusion on the upper part of the needle 2. A recess 58a for fitting the ring 60 provided on the needle 2 is provided on the upper surface of the tip end portion of the needle holding arm 58. The needle holding arm 58 holds the needle 2 with the ring 60 fitted in the recess 58a.

Figure 11:
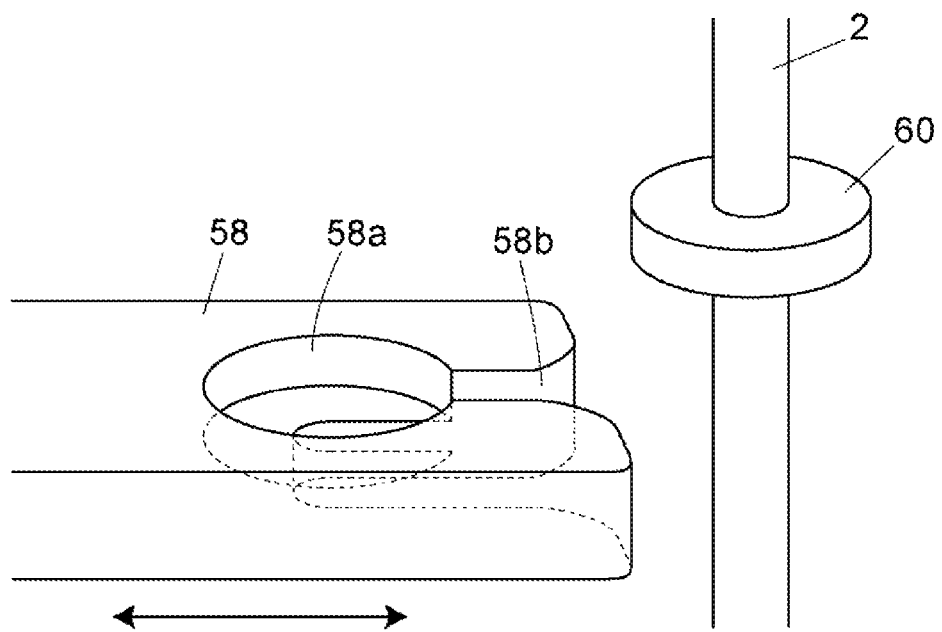
FIG. 11 is a perspective view showing an example of a configuration of a needle holding arm.
Figure 12:
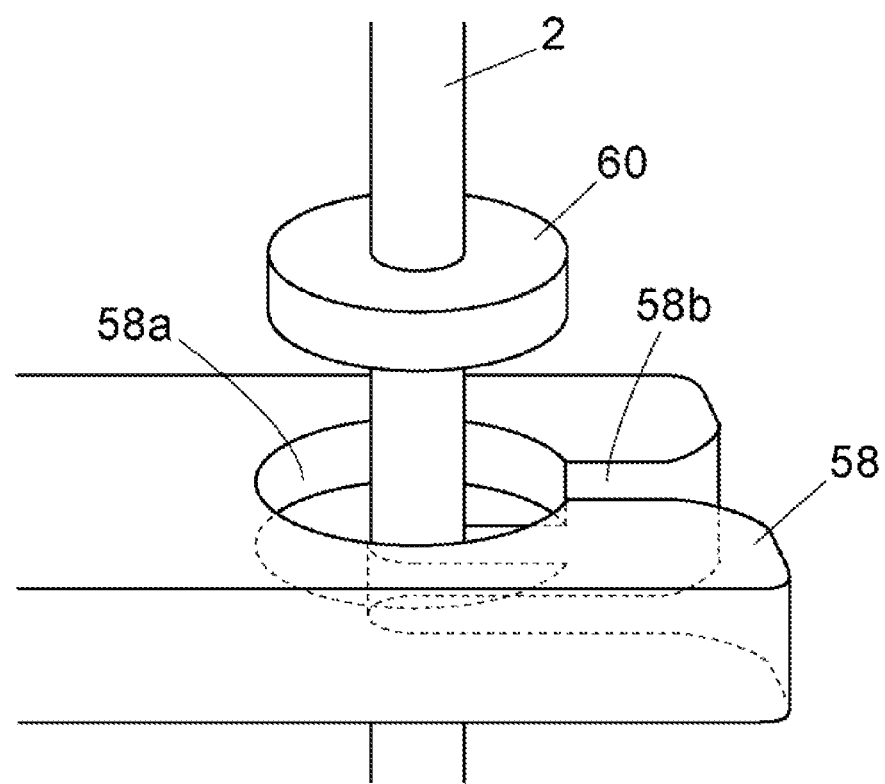
FIG. 12 is a view showing a state at the time of attaching/detaching the needle with a needle holding arm.

As shown in FIG. 11, an opening 58*b* (cutout) having a width slightly larger than the outer diameter of the needle 2 is provided on one side of the needle holding arm 58. The opening 58*b* extends to the center of the recess 58*a*. When mounting the needle 2 on the needle holding arm 58, the needle holding arm 58 is moved in the horizontal direction below the ring 60 of the needle 2 until the needle 2 reaches the center of the recess 58*a* through the opening 58*b*. Then, as shown in FIG. 12, after the needle 2 has reached the center of the recess 58*a*, the needle holding arm 58 is raised to fit the ring 60 in the recess 58*a*.

Conversely, when detaching the needle 2 from the needle holding arm 58, after inserting the lower part of the needle 2 into the vertical hole of the needle setting unit 76, the needle holding arm 58 is lowered until the needle holding arm 58 becomes lower than the ring 60, and the needle holding arm 58 is moved in the horizontal direction to pull the needle 2 out of the opening 58*b* of the needle holding arm 58.

With the above configuration, the attachment/detachment of the needle 2 can be automatically performed by the needle holding arm 58. As a result, the apparatus can automatically replace the needle 2 with an appropriate needle 2 so as to use, for example, a needle 2 having an internal capacity depending on the sample injection volume set by the user.

DESCRIPTION OF REFERENCE SYMBOLS

1: autosampler
2: needle
2*a*: needle lower end portion
2*b*: needle upper end portion
4: needle driving mechanism
6: sample container
8: syringe pump
10: syringe flow path
12: first adapter
14: first adapter driving mechanism
16: switching valve
18: injection port
20: mobile-phase liquid-delivery flow path
22: second adapter
24: second adapter driving mechanism
26: mobile phase supply flow path
28: liquid feed pump
30: analysis flow path
32: analytical column
34: detector
36: control unit
38: sampling operation unit
40: needle movement operation unit
42: injecting operation unit
44: horizontal moving unit
46, 52, 64: ball screw
48, 54, 66, 74: motor
50: first horizontal arm
56: second horizontal arm
58: needle holding arm
58*a*: recess
58*b*: opening
60: ring
62: ball screw support portion
68: second adapter holding arm
70: rotation shaft
72: first adapter holding arm
76: needle setting unit

The invention claimed is:

1. An autosampler comprising:
a needle having a capacity to retain a sample therein, both ends of the needle each being formed in a pointed shape;
a needle driving mechanism configured to move the needle in a vertical direction and in a horizontal plane direction in a state in which the needle is held in the vertical direction;
an injection port having an opening opened upward for allowing an insertion of a lower end of the needle and configured to connect the needle with the lower end of the needle inserted into the opening;
a syringe pump configured to suck and discharge a liquid;
a first adapter having an opening communicated with a suction/discharge opening of the syringe pump and opened downward for allowing an insertion of an upper end of the needle, the first adapter being configured to connect the needle with the upper end of the needle inserted in the opening to communicate the syringe pump and the needle;
a mobile-phase liquid-delivery flow path configured to deliver a mobile phase;
a second adapter connected to the mobile-phase liquid-delivery flow path and having an opening opened downward for allowing an insertion of the upper end of the needle, the second adapter being configured to connect the needle with the upper end of the needle inserted into the opening to communicate the mobile-phase liquid-delivery flow path and the needle;
a first adapter driving mechanism configured to perform attachment/detachment of the first adapter with respect to the upper end portion of the needle by moving the first adapter above the needle in the vertical direction;
a second adapter driving mechanism configured to perform attachment/detachment of the second adapter with respect to the upper end portion of the needle by moving the second adapter above the needle with the lower end of the needle inserted in the injection port;
a switching mechanism configured to switch whether a liquid feeding device for feeding the mobile phase is connected to the mobile-phase liquid-delivery flow path and whether an analysis flow path communicated with an analytical column which separates the sample the sample by a component and the injection port are connected, the switching mechanism having an injecting mode in which a connection of the liquid feeding device to the mobile-phase liquid-delivery flow path and a communication of the analysis flow path and the injection port are performed simultaneously; and
a control unit configured to control the needle driving mechanism, the syringe pump, the first adapter driving mechanism, the second adapter driving mechanism, and the switching mechanism,
wherein the control unit includes
a sampling operation unit configured to connect the upper end of the needle to the first adapter while inserting the lower end of the needle into a sample container containing the sample to be sucked and perform a sampling operation of sucking the sample into the needle by the syringe pump,
a needle movement operation unit configured to perform a needle movement operation of connecting the lower end of the needle to the injection port in a state in which the upper end of the needle is connected to the first adapter after the sampling operation, and an injecting operation unit configured to perform an injecting operation of detaching the first adapter from the needle upper end, connecting the second adapter to the needle upper end, and performing an injecting operation of changing the switching mechanism to the injecting mode after the needle movement operation.

2. The autosampler as recited in claim 1,
wherein the needle driving mechanism includes a needle holding unit to detachably hold the needle.

3. The autosampler as recited in claim 2,
further comprising a needle setting unit configured to set a plurality of needles different in internal capacity,
wherein the needle driving mechanism is configured to hold one of needles installed in the needle setting unit depending on a sample injection volume to the analysis flow path by the needle holding unit.

4. The autosampler as recited in claim 2, wherein
the needle is provided with a protrusion protruding in a peripheral direction on an outer peripheral surface of the needle, and
the needle holding unit has a recess for holding the needle by fitting the protrusion from above to an upper surface and a cutout formed from a side surface to a center of the recess and having a width larger than an outer diameter of the needle and smaller than an inner diameter of the recess.

5. The autosampler as recited in claim 1, wherein
the second adapter driving mechanism is a mechanism configured to move a second adapter in the vertical direction above the injection port, and
the first adapter driving mechanism includes a mechanism for moving the first adapter in the vertical direction above the needle and a mechanism for retracting the first adapter from above the needle when the lower end of the needle is connected to the injection port.

* * * * *